United States Patent [19]

Miyoshi et al.

[11] Patent Number: 4,622,074

[45] Date of Patent: Nov. 11, 1986

[54] PIGMENTS AND EXTENDER PIGMENTS WHICH ARE SURFACE-TREATED WITH HYDROGENATED LECITHIN, AND COSMETICS CONTAINING THE SAME

[75] Inventors: Ryota Miyoshi, Yono; Isao Imai, Kuki, both of Japan

[73] Assignee: Miyoshi Kasei Co., Ltd., Saitama, Japan

[21] Appl. No.: 729,730

[22] Filed: May 2, 1985

[51] Int. Cl.[4] .............................................. C08J 7/00
[52] U.S. Cl. ........................ 106/308 F; 106/288 R; 106/308 M
[58] Field of Search ............ 106/288 R, 308 F, 308 M

[56] References Cited

U.S. PATENT DOCUMENTS

| | | | |
|---|---|---|---|
| 3,085,100 | 4/1963 | Chang | 106/308 F |
| 4,305,853 | 12/1981 | Kronstein et al. | 106/308 F |
| 4,371,642 | 2/1983 | Jaffe | 106/308 M |
| 4,478,968 | 10/1984 | Jaffe | 106/308 M |
| 4,548,968 | 10/1985 | Jaffe | 106/308 M |

Primary Examiner—Lorenzo B. Hayes
Assistant Examiner—Willie J. Thompson
Attorney, Agent, or Firm—Armstrong, Nikaido, Marmelstein & Kubovcik

[57] ABSTRACT

Pigments or extender pigments the surface of which are uniformly coated with hydrogenated lecithin or with the reaction product of hydrogenated lecithin and a metal salt; and a composition for make-up cosmetics containing such pigments or extender pigments and exhibiting excellent protection for the skin, resistance to wear, and good water repellency.

5 Claims, No Drawings

PIGMENTS AND EXTENDER PIGMENTS WHICH ARE SURFACE-TREATED WITH HYDROGENATED LECITHIN, AND COSMETICS CONTAINING THE SAME

BACKGROUND OF THE INVENTION

The present invention relates to new pigments or extender pigments the surfaces of which are uniformly coated with hydrogenated lecithin which is adsorbed onto said surfaces, and make-up cosmetics containing such pigments or extender pigments.

In order to improve the "wear" of make-up and prevent its disruption by skin perspiration, make-up cosmetics such as powder foundation, rouge, and eye shadow, have been prepared with pigments or extender pigments which are made water repellent by coating the surfaces of the pigments or extender pigments with organo-silicone derivatives or metallic soap, or in the alternative, metallic soap itself is added to the cosmetics.

However, the addition of a large amount of metallic soap to the bulk of the cosmetics does not impart sufficient water repellency, and furthermore causes skin irritation and makes the color of the cosmetic dull.

Make-up cosmetics prepared with pigments the surfaces of which are treated with metal soap are somewhat improved with respect to these defects, but are not perfect. Their spreading, extendability, and feel to the skin remain unsatisfactory.

Some make-up cosmetics have been used which include pigments treated with organosilicone derivatives. These pigments are excellent in water repellency and spreading, but have defects such as inferior adhesion to the skin, a tendency to dry the skin and to feel coarse. Using lecithin in make-up cosmetics has been proposed. However, the simple mixing of lecithin powder with pigments causes the pigments to change in color and odor. Further, due to insufficient water repellency, the wear of this make-up is not satisfactory.

SUMMARY OF THE INVENTION

An object of the present invention is to provide pigments or extender pigments characterized by excellent protection of the skin from pollution, good water repellency, and a smooth texture, more specifically pigments or extender pigments the surfaces of which are uniformly coated with hydrogenated lecithin.

Another object of the present invention is to provide compositions for make-up cosmetics which are smooth, spread well, have a moisturizing effect on the skin and causes no skin irritation; more specifically, compositions for make-up cosmetics which contain pigments or extender pigments the surfaces of which are uniformly coated with hydrogenated lecithin.

These and other objects and features of the present invention will be apparent from the following detailed description of the invention, it being understood that variations and modifications may be made therein without departing from the spirit of the invention.

DETAILED DESCRIPTION OF THE INVENTION

The pigments or extender pigments of this invention have surfaces which are uniformly coated with hydrogenated lecithin which is adsorbed onto said surfaces. The make-up cosmetics of this invention contain such pigments or extender pigments.

Lecithin is an oily substrate, and it is not possible to coat a pigment with lecithin. However, hydrogenated lecithin is a powder which, according to the present invention, can provide a uniform coating on a pigment.

The hydrogenated lecithins which can be used in the present invention are: (1) hydrogenated synthetic lecithin; and (2) hydrogenated natural lecithin obtained by extraction of lecithin from egg yolk, soy bean, corn and rapeseed oil followed by hydrogenation. The iodine value of the hydrogenated lecithin should be less than 30.

The lecithin to be hydrogenated for use in this invention must be of good quality and must not be oxidized and/or changed in color.

The lecithin which can be used in the present invention does not have to be pure phosphatidyl choline, but can contain other phospholipids such as phosphatidyl ethanolamine, phosphatidyl serine, phosphatidyl inositol, and also neutral fat from egg yolk, soy bean, corn or rapeseed. The term "lecithin" refers to the overall composition which may contain other phospholipids and neutral fat in addition to phosphatidyl choline.

Most phospholipids have a tendency to oxidize easily (because they are mostly unsaturated fatty acids) and emit an unpleasant odor as a result of the oxidation. For that reason, it has been necessary to use lecithin which is hydrogenated and thereby stabilized.

When hydrogenated egg yolk lecithin having an iodine value of less than 30 is used for treating the surfaces of pigments, cosmetics prepared with such pigments presented no problems with odor or change in color, and performed excellently as make-up cosmetics.

The pigments which can be coated uniformly with hydrogenated lecithin according to this invention are inorganic pigments and organic pigments. Examples of such pigments are: titanium dioxide, zinc oxide, zirconium dioxide, red iron oxide, yellow iron oxide, black iron oxide, ultramarine blue, Prussion blue, chromium oxide, chromium hydroxide. Examples of extender pigments are: talc, kaolin, muscovite mica, sericite, other micas, magnesium carbonate, calcium carbonate, aluminum silicate, magnesium silicate, calcium silicate, clay, titanated mica, bismuth oxychloride, silica beads, plastic beads such as acryl, tar dyestuff and natural dyestuff.

An example of a method for treating the surfaces of pigments and extender pigments with hydrogenated lecithin follows. The pigments or extender pigments to be treated are dispersed in water. Then the hydrogenated lecithin is added in a proportion of 0.3 to 10% by weight of hydrogenated lecithin, and the mixture is stirred vigorously with heating until it is completely dissolved or emulsified.

At this point, a portion of the hydrogenated lecithin is adsorbed on the surface of the pigments. In order to complete the adsorption of hydrogenated lecithin, a 1–30% by weight aqueous solution of water soluble salts of Al, Mg, Ca, Zn, Zr and Ti is added dropwise, in sufficient amount to give a proportion of 0.1–2 equivalent of salt to hydrogenated lecithin. Examples of such metal salts are aluminum sulfate, aluminum chloride, aluminum nitrate, aluminum potassium sulfate, magnesium chloride, magnesium sulfate, magnesium nitrate, magnesium potassium sulfate, calcium chloride, calcium nitrate, calcium acetate, zinc chloride, zinc nitrate, zinc sulfate, zinc acetate, zirconium sulfate, zirconium chloride, titanium oxysulfate, and titanium chloride. The added metal salt reacts with hydrogenated lecithin to form a water insoluble reaction product which adsorbs perfectly onto the surfaces of the pigments and extender pigments. According to this invention, neutral fat (such as egg yolk oil and other oils) adsorbs simultaneously with the metal salt of hydrogenated lecithin onto the surfaces of the pigments and extender pigments. The desired treated pigment or treated extender pigment is obtained after removing water from the reaction mixture in a centrifuge, and drying at 80°–120° C. The amount of hydrogenated lecithin adsorbed depends on the size of the pigment particles. A thicker coating is usually obtained with particles of a smaller size.

The treated pigments or treated extender pigments thus obtained, the surfaces of which are uniformly coated with hydrogenated lecithin, provide excellent protection to the skin, have good water repellency, and feel good to the touch. Being biochemically similar to the skin because of the presence of the lecithin, these treated pigments or extender pigments are particularly compatible with the skin.

The cosmetic compositions which contain such treated pigments or extender pigments are smooth, spread well, have a good moisturizing effect and good water repellency, prevent drying of the skin, are non-irritant, provide protection against sun rays, and give long lasting make-up.

It is particularly advantageous to use these treated pigments or extender pigments without drying them. In that case, after the hydrogenated lecithin is adsorbed on the surfaces of the pigments in the water phase, the paste obtained is partially dehydrated in a centrifuge, packed in a plastic bag and sterilized by placing the plastic bag in boiling water. This paste, which is not dried, is mixed with the base of the liquid or paste make-up cosmetic being prepared, such as a water-based foundation, or a paste foundation.

The treated pigment, on the surface of which hydrogenated lecithin is adsorbed, contains much water. Accordingly, the dehydrated paste obtained after centrifugation is easily dispersed into other water systems or emulsion systems, and is easily redispersed after precipitation without the application of any particularly strong force or the addition of large amounts of surfactants which may cause skin irritation. Skin application of the water-dispersed or emulsion type make-up cosmetics thus obtained results in strong and even adhesion to the skin.

Treated pigments applied in this way on the skin lose water due to airdrying and leave very highly hydrophobic particles which are not rewetted by water. Thus excellent make-up cosmetics are obtained, which moisturize the skin, are non-irritant to the skin and remain effective for a long period.

Examples of make-up compositions according to the present invention are powder foundation, rouge, and eye shadow.

The present invention is further described in greater detail in the following examples.

EXAMPLE 1

1 kg of sericite was added to 5 liters of water which was stirred vigorously to disperse the sericite uniformly therein. 10 g of hydrogenated lecithin (phospholipid content of 60%, iodine value of 28) was added to the mixture which was heated at 70° C. until the lecithin was completely in suspension. Then 80 ml of a 20 wt. % aqueous solution of $Al_2(SO_4)_3$ was added dropwise to the mixture for 10 minutes, and further stirring was carried out for another 10 minutes. The resulting paste of treated sericite was dehydrated in a centrifuge, crushed and dried at 105° C. for 16 hours to produce the treated extender pigment.

Treated sericite obtained in this way had a strong water repellency, extreme smoothness and moisturizing effect and did not feel coarse when applied to the skin. Thus, is was found ideal as an extender pigment for make-up cosmetics.

COMPARISON EXAMPLE 1

100 g of sericite was added to 0.5 liter of water which was vigorously stirred to disperse the sericite uniformly therein. 1 g of potassium myristate was added to the suspension and dissolved completely. Then, 10 ml of a 20 wt. % aqueous solution of $ZnSO_4$ was added dropwise to the suspension for 10 minutes, and further stirring was carried out for another 10 minutes.

The suspension was filtered by a suction method. The resulting block was finely crushed and dried at 105° C. for 10 hours. Extender pigments treated with metallic soap by the above described method exhibited good adhesion to skin, but were inferior to extender pigments treated with hydrogenated lecithin with respect to spreading and water repellency.

COMPARISON EXAMPLE 2

1.5 g of methyl hydrodienepolysiloxane was dissolved completely in 15 g of benzene, then 50 g of sericite was added to the solution which was stirred in a mixer for 5 minutes. The mixture was air-dried at room temperature to remove the benzene completely, then baked at 120° C. for 3 hours. Silicone-treated sericite thus obtained had almost no unpleasant odor and exhibited good water repellency and fluidity. But the powder felt very dry, causing the skin to feel very coarse, and it had poor adhesion to the skin.

EXAMPLE 2

1 kg of talc was added to 4 liters of water which was stirred vigorously to disperse the talc uniformly therein. Then 20 g of hydrogenated soybean lecithin (phospholipid content of 30 wt. % iodine value of 5) was dissolved in 1 liter of hot water and the resulting solution was added to the above dispersion of talc in water.

Then 100 ml of a 20 wt. % aqueous solution of $Al(NO_3)_3$ was dripped into the pigment suspension for 10 minutes, and further stirring was carried out for another 10 minutes.

The treated extender pigment was dehydrated in a centrifuge, then dried at 105° C. for 16 hours in heated air. Treated talc thus obtained was slightly yellowish, exhibited stong hydrophobicity and outstanding smoothness, and felt wet and soft to the touch.

EXAMPLE 3

Mica, titanated mica, titanium dioxide, yellow iron oxide, red iron oxide, and black iron oxide were treated individually as follows.

1 kg of each of the above pigments or extender pigments was added to 4 liters of water and dispersed uniformly therein. Meanwhile, 30 g of hydrogenated lecithin (phospholipid content of 30 wt. %, iodine value of 5) was dissolved in 1 liter of hot water, and the resulting hot solution was added to the above dispersion of pigment or extender pigment in water. 100 ml of a 20 wt. % aqueous solution of $Al(NO_3)_3$ was added dropwise to the dispersion of pigment or extender pigment and hydrogenated lecithin for 10 minutes, and further stirring was carried out for another 10 minutes. Then the pigment or extender pigment was subjected to centrifugal dehydration and dried at 105° C. for 16 hours to produce treated mica, treated titanated mica, treated titanium dioxide, treated yellow iron oxide, treated red iron oxide and treated black iron oxide.

Treated pigments or extender pigments thus obtained exhibited strong hydrophobicity, smoothness, and moisturizing effect, and felt excellent to the touch. Thus, these pigments and extender pigments were ideal for make-up cosmetics.

EXAMPLE 4 AND COMPARATIVE EXAMPLE 3

A powdery foundation having the following formulation was prepared.

| Component 1 | |
|---|---|
| Treated sericite obtained in Example 1 | 50.0 wt. parts |
| Treated talc of Example 2 | 8.1 |
| Treated mica of Example 3 | 3.0 |
| Treated titanated mica of Example 3 | 3.0 |
| Treated titanium dioxide of Example 3 | 19.0 |
| Treated yellow iron oxide of Example 3 | 3.0 |
| Treated red iron oxide of Example 3 | 1.0 |
| Treated black iron oxide of Example 3 | 0.2 |
| Component 2 | |
| Squalane | 50.0 wt. parts |
| Methylpolysiloxane | 3.0 |
| Isopropyl myristate | 2.0 |
| Paraffin | 1.0 |
| Surfactant | 1.0 |
| Preservatives | 1.0 |
| Perfume | 0.5 |

Component 1 was mixed in a Henschel mixer, then crushed in an atomizer. Component 2 was mixed with heating and poured into crushed component 1. The mixture was processed in the Henschel mixer again and crushed in an atomizer. The crushed mixture was molded to give the end products.

The powdery foundation thus made had excellent hydrophobicity, and could be applied either with a dry sponge or a sponge dampened with water.

The powdery foundation using the pigments and extender pigments of the present invention was compared to a foundation comprising identical materials and made by the same process as described above, except that the component 2 was added to pigments and extender pigments which had been treated with methylhydrodienepolysiloxane by the method of comparison Example 2. The powder foundation using the pigments and extender pigments of the invention was found to be much superior with respect to ease of transfer to a sponge, adhesion to the skin, spreading on the skin, smoothness and long-lasting wear after application.

COMPARISON EXAMPLE 4

A powdery foundation having the following formulation was prepared.

| Component 1 | |
|---|---|
| Sericite | 49.0 wt. parts |
| Talc | 8.1 |
| Mica powder | 3.0 |
| Titanated mica | 3.0 |
| Titanium dioxide | 19.0 |
| Yellow iron oxide | 3.0 |
| Red iron oxide | 1.0 |

| -continued | |
|---|---|
| Black iron oxide | 0.2 |
| Component 2 | |
| Squalane | 4.0 wt. parts |
| Methylpolysiloxane | 3.0 |
| Isopropyl mirystate | 2.0 |
| Paraffin | 1.0 |
| Soybean lecithin (phospholipid content 30%, iodine value 90) | 3.0 |
| Preservatives | 0.2 |
| Perfume | 0.5 |

Component 1 was mixed in a Henschel mixer, and crushed in an atomizer. Then component 2 was mixed with heating and poured into the above crushed component 1. The mixture was processed in the Henschel mixer again and crushed in the atomizer. The crushed mixture was molded to give the final products. The powdery foundation thus made felt smooth but did not give a long-lasting make-up. In addition, one month later, the color of the powdery foundation turned to pale brown and some odor was generated from it.

EXAMPLE 5A 450 g of sericite, 200 g of mica powder, 120 g of talc, 100 g of kaolin, 90 g of $TiO_2$, 20 g of yellow iron oxide and 20 g of red iron oxide (adding up to 1 kg in total weight) was suspended in 4 liters of water. To the suspension 30 g of hydrogenated soybean lecithin (phospholipid content of 30%, iodine value of 5) was added and the suspension was stirred thoroughly. 80 ml of a 15 wt. % aqueous solution of zinc sulfate was added dropwise to the suspension over 10 minutes. Then further stirring was carried out for another 10 minutes.

The suspension was dehydrated in a centrifuge. The paste thus obtained was sterilized by heating for 30 minutes in boiling water at 100° C. to produce 2.2 kg of a paste cake with 50 wt. % water content.

EXAMPLE 5B

Foundation

| Component 1 | |
|---|---|
| Treated pigment of Example 5A | 40.0 wt. parts |
| Mineral oil | 3.5 |
| Squalane | 5.0 |
| Stearyl alcohol | 3.0 |
| Lanolin | 1.0 |
| Surfactant | 1.5 |
| Preservative | 0.2 |
| Component 2 | |
| Propylene glycol | 5.0 |
| Ion exchange water | 40.0 |
| Perfume | 0.8 |

Each of components 1 and 2 was separately heated up to 70° C., respectively. Component 2 was added over five minutes into component 1 which was being stirred by means of a homogenizer. Thereafter, further stirring was carried out for another 10 minutes to emulsify the mixture. Then the resulting suspension was cooled and charged into containers to give the final products.

The above described foundation was an excellent cosmetic having strong adhesion to the skin, and giving a long-lasting uniform make-up finish.

Egg lecithin was used in the examples described above. However, the lecithin which can be used in this invention is not particularly limited. For example, soy bean lecithin can be used. The phospholid contents (%)

of commercially available egg lecithin and soy bean lecithin are indicated below.

| Phospholipids | egg yolk | soybean |
|---|---|---|
| Phosphatidyl choline | 73.0 wt. parts | 29.4 wt. parts |
| Phosphatidyl ethanolamine | 14.9 | 16.5 |
| Phosphatidyl serine | 0.2 | 12.1 |
| Phosphatidyl inositol | 0.5 | 13.0 |
| Phosphatidic acid | 0.7 | 6.7 |
| Polyglycerophosphatidic acid | — | 2.7 |
| Plasmalogen | 1.0 | 0.6 |
| Sphingomyelin | 2.5 | 3.5 |

What is claimed is:

1. A pigment or extender pigment the surfaces of which are uniformly coated with of a layer of adsorbed hydrogenated lecithin or with a layer of adsorbed reaction product of hydrogenated lecithin with a water-soluble metal salt, said hydrogenated lecithin having an iodine value of less than 30.

2. The pigment or extender pigment according to claim 1, wherein the hydrogenated lecithin is natural lecithin which has been extracted from egg yolk, soybean, corn or rapeseed and dehydrogenated.

3. The pigment or extender pigment according to claim 1, wherein the water-soluble metal salt is selected from the group consisting of salts of Al, Mg, Ca, Zn, Zr and Ti.

4. The pigment or extender pigment according to claim 1, wherein the pigment or extender pigment is selected from the group consisting of inorganic pigment, organic extender, and extender pigment.

5. The pigment or extender pigment according to claim 1, wherein the pigment or extender pigment is coated with 0.3 to 10% by weight of hydrogenated lecithin.

* * * * *